US012508168B2

(12) United States Patent
Colleran

(10) Patent No.: US 12,508,168 B2
(45) **Date of Patent: *Dec. 30, 2025**

(54) ARM SLEEVE THAT PROVIDES ASSISTANCE DURING AN ARM MOTION

(71) Applicant: Jason Colleran, Roswell, GA (US)

(72) Inventor: Jason Colleran, Roswell, GA (US)

( * ) Notice: Subject to any disclaimer, the term of this patent is extended or adjusted under 35 U.S.C. 154(b) by 705 days.

This patent is subject to a terminal disclaimer.

(21) Appl. No.: 17/839,425

(22) Filed: Jun. 13, 2022

(65) Prior Publication Data

US 2022/0331169 A1 Oct. 20, 2022

Related U.S. Application Data

(63) Continuation of application No. 16/512,339, filed on Jul. 15, 2019, now Pat. No. 11,369,523.

(60) Provisional application No. 62/698,388, filed on Jul. 16, 2018.

(51) Int. Cl.
*A61F 13/10* (2006.01)
*A41D 27/10* (2006.01)

(52) U.S. Cl.
CPC ............ *A61F 13/101* (2013.01); *A41D 27/10* (2013.01)

(58) Field of Classification Search
CPC .............. A61F 13/10–102; A61F 13/14; A61F 13/146; A61F 5/01–0104; A61F 5/0118; A61F 5/04; A61F 5/05; A61F 5/058; A61F 5/05841; A61F 5/05858; A61F 5/37; A61F 5/3715–3738; A41D 27/10; A41D 13/05; A41D 13/0512; A41D 13/0518; A41D 13/055–0575; A41D 13/08; A41D 31/00; A41D 31/04; A41D 31/18; A41D 31/185
See application file for complete search history.

(56) References Cited

U.S. PATENT DOCUMENTS

| | | | | |
|---|---|---|---|---|
| 3,000,378 | A | 9/1961 | Zieman | |
| 3,785,371 | A | 1/1974 | Lewis | |
| 4,229,833 | A | 10/1980 | Cox et al. | |
| 4,344,189 | A * | 8/1982 | Futere | A41D 13/08 2/16 |
| 4,910,802 | A | 3/1990 | Malloy | |

(Continued)

FOREIGN PATENT DOCUMENTS

| | | |
|---|---|---|
| GB | 2571735 A | 9/2019 |

*Primary Examiner* — Michelle J Lee

(74) *Attorney, Agent, or Firm* — Asgaard Patent Services, LLC; F. Wayne Thompson, Jr.

(57) ABSTRACT

Implementations of an arm sleeve that provides external assistance to an arm and shoulder of a user during an arm motion are provided. In one implementation, the arm sleeve comprises a framework that includes a torso portion configured to be attached to the torso of the user and an arm portion configured to receive at least a portion of the arm of the user. The framework of the arm sleeve is a unitary construction of interconnected elastic members. The interconnected elastic members include a first elastic member configured to play an active part throughout an overhead throwing motion, a second elastic member configured to decrease the concentric contraction force necessary for shoulder abduction during the cocking phase of a throwing motion, and a third elastic member configured to assist eccentrically contracting muscles during the deceleration phase of a throwing motion. In another implementation, the framework of the arm sleeve is encased by an elastomeric cover.

19 Claims, 13 Drawing Sheets

(56) References Cited

U.S. PATENT DOCUMENTS

| | | | |
|---|---|---|---|
| 4,911,728 | A | 3/1990 | Rigel |
| 4,993,705 | A | 2/1991 | Tolle |
| 5,063,913 | A | 11/1991 | Nyi |
| 5,168,577 | A | 12/1992 | Detty |
| 5,176,600 | A | 1/1993 | Wilkinson |
| 5,188,587 | A | 2/1993 | McGuire et al. |
| 5,306,222 | A | 4/1994 | Wilkinson |
| 5,403,002 | A | 4/1995 | Brunty |
| 5,570,472 | A | 11/1996 | Dicker |
| 5,628,725 | A | 5/1997 | Ostergard |
| 5,720,042 | A | 2/1998 | Wilkinson |
| 5,737,772 | A | 4/1998 | Dicker et al. |
| 5,737,773 | A | 4/1998 | Dicker et al. |
| 5,745,917 | A | 5/1998 | Dicker et al. |
| 5,819,322 | A | 10/1998 | Dicker et al. |
| 5,857,947 | A | 1/1999 | Dicker et al. |
| 5,891,079 | A | 4/1999 | Barnes |
| 5,925,010 | A | 7/1999 | Caprio, Jr. |
| 5,937,442 | A | 8/1999 | Yamaguchi et al. |
| 5,978,966 | A | 11/1999 | Dicker et al. |
| 5,993,362 | A | 11/1999 | Ghobadi |
| 6,106,493 | A | 8/2000 | Rozell |
| 6,685,662 | B1 | 2/2004 | Curry et al. |
| 6,709,411 | B1 | 3/2004 | Olinger |
| 7,074,202 | B1 | 7/2006 | Weber et al. |
| 7,563,212 | B2 | 7/2009 | Smith |
| 7,608,026 | B1 | 10/2009 | Nicassio |
| 8,216,170 | B2 | 7/2012 | Ingimundarson et al. |
| 8,287,478 | B2 | 10/2012 | Ostergard et al. |
| 8,601,613 | B2 | 12/2013 | Melhart |
| 8,667,613 | B2 | 3/2014 | Blakely et al. |
| D849,255 | S | 5/2019 | Colleran |
| 10,772,782 | B2 | 9/2020 | Lebolt et al. |
| 2004/0107479 | A1 | 6/2004 | Dicker et al. |
| 2006/0026732 | A1 | 2/2006 | Nordt, III et al. |
| 2006/0070165 | A1 | 4/2006 | Nordt, III et al. |
| 2010/0088803 | A1 | 4/2010 | Orloff |
| 2010/0285936 | A1 | 11/2010 | Tacker et al. |
| 2012/0041352 | A1 | 2/2012 | Ostergard |
| 2012/0210487 | A1 | 8/2012 | Albin et al. |
| 2012/0210488 | A1 | 8/2012 | Blakely et al. |
| 2014/0058304 | A1 | 2/2014 | Ex-Lubeskie et al. |
| 2016/0135525 | A1 | 5/2016 | Colleran |
| 2016/0213504 | A1 * | 7/2016 | Colleran .............. A41D 31/185 |
| 2018/0116893 | A1 * | 5/2018 | Lebolt ................... A61F 5/0104 |
| 2018/0249775 | A1 | 9/2018 | Pitchforth et al. |

* cited by examiner

ARM SLEEVE THAT PROVIDES ASSISTANCE DURING AN ARM MOTION

CROSS-REFERENCE TO RELATED APPLICATIONS

This is a continuation application claiming the benefit of U.S. patent application Ser. No. 16/512,339, filed on Jul. 15, 2019, which claims the benefit of U.S. Provisional Application Ser. No. 62/698,388, filed on Jul. 16, 2018, the entireties of both applications are incorporated herein by reference.

TECHNICAL FIELD

This disclosure relates to implementations of an arm sleeve that provides external assistance to the arm and shoulder during an arm motion.

BACKGROUND

An arm motion, such as an overhead throwing motion when pitching a baseball, generally involves a winding-up motion, an acceleration of the arm, release of the ball, and a follow-through. When the arm is accelerating and following through, valgus and varus torque are generated, thereby placing a valgus and a varus force on the elbow joint, in particular, the soft medial structures of the elbow including the medial collateral ligament, otherwise known as the ulnar collateral ligament (UCL).

Placing large valgus and varus loads, such as through repeated hard throwing or pitching, on the elbow can lead to injury of the UCL, including over-stretching, fraying, and tearing. The UCL may become injured either by acute ligament tears, or merely through overuse and repetitive stress. For example, repeated valgus and varus stresses from repetitive throwing may result in overuse injury where the tissue breakdown exceeds the tissue's ability to repair itself. In children, such repetitive stress may manifest as "little league elbow" which can lead to medial epicondylar apophysitis and stress fractures through the medial epicondylar epiphyses.

Injury to the UCL can be particularly problematic because the UCL, along with the lateral collateral ligament, is the main source of stability for the elbow. When the UCL is damaged or injured and does not heal correctly, the elbow can become loose and/or unstable, leading to further injury. This may lead to the need for corrective surgery, such as Tommy John surgery, to repair the UCL.

Previous attempts at preventative or rehabilitation devices or garments have focused on either compression, such as a tight-fitting sleeve over the elbow, or braces designed to provide support and/or limit the arm motion. However, such prior approaches are focused on trying to provide structural support for the elbow, rather than providing positive assistance to the muscles in the arm and shoulder that help stabilize the UCL in order to reduce the valgus and varus load.

Accordingly, it can be seen that a need exists for the arm sleeve that provides external assistance to the arm and shoulder during an arm motion disclosed herein. It is to the provision of an arm sleeve configured to address these needs, and others, that the present invention is primarily directed.

SUMMARY

Implementations of an arm sleeve that provides external assistance to an arm and shoulder of a user during an arm motion, such as a throwing motion, are provided. In one implementation, the arm sleeve comprises a framework that includes a torso portion configured to be attached to the torso of the user and an arm portion configured to receive at least a portion of the arm of the user. The framework is a unitary construction of interconnected elastic members.

The interconnected elastic members of the framework include a first elastic member configured to store and release elastic energy to assist muscles of the user. The first elastic member includes a first end, a second area, and a second end. The first end of the first elastic member extends from a front side of the torso portion, across a front side of the arm portion to the second area, which is part of the arm portion. The first elastic member is configured to continue directly from the second area to spiral posteriorly across a triceps area of the arm, past an elbow joint of the arm, and anteriorly to the second end, which is located near a distal end of the arm portion at a mid-forearm of the arm when the arm sleeve is being worn.

The interconnected elastic members of the framework include a second elastic member with a first end and a second end. The first end of the second elastic member extends from an edge of the torso portion that is configured to overlay the shoulder of the arm to the second end, which is part of the arm portion and superior to the bicep of the arm when the arm sleeve is being worn.

The interconnected elastic members of the framework include a third elastic member with a first end and a second end. The first end of the third elastic member extends from a back side of the torso portion, across a back side of the arm portion to the second end. The second end is part of the arm portion and is joined to the second area of the first elastic member.

Each of the first elastic member and the third elastic member extends separately from the front side and the back side of the torso portion, respectively, and converges at the second area. In addition, the first elastic member and the third elastic member are fixed relative to each other at the second area.

In another implementation, the framework of the arm sleeve is encased by an elastomeric cover. Methods of use and other implementations are also provided. It is intended that all such additional implementations and methods described in the detailed description be within the scope of the invention, and be protected by the accompanying claims.

BRIEF DESCRIPTION OF THE DRAWINGS

Like reference numerals refer to corresponding parts throughout the several views of the drawings.

DETAILED DESCRIPTION

As discussed above, an arm motion, such as an overhead throwing motion when pitching a baseball, generally involves a winding-up motion, an acceleration of the arm, release of the ball, and a follow-through. Other similar arm motions may include a swinging motion, such as during tennis, handball, and volleyball, that generally involves a winding-up motion, an acceleration of the arm, hitting the ball, and a follow-through. When the arm is accelerating and following through, valgus and varus torque are generated, thereby placing a valgus and a varus force on the elbow joint, in particular, the soft medial structures of the elbow including the medial collateral ligament, otherwise known as the ulnar collateral ligament (UCL).

FIGS. 1A-1C and 2A-2B illustrate an example implementation of an arm sleeve 100 according to the principles of the present disclosure. The arm sleeve 100 is configured to decrease elbow joint forces present at the end-range cocking phase of an overhead throwing motion. More specifically, the arm sleeve 100 decreases the distraction force on the medial side of the elbow and the compressive force on the lateral side of the elbow. The arm sleeve 100 is also configured to assist with the initiation of the acceleration phase of an overhead throwing motion by providing elastic assistance to the shoulder joint. Further, the arm sleeve 100 is configured to provide elastic resistance during the deceleration and follow-through phase of an overhead throwing motion, decreasing the eccentric contraction demands of the shoulder's external rotators. A first elastic member, a second elastic member, and a third elastic member of a framework of the arm sleeve 100 are operable to provide assistance to at least one muscle supporting an ulnar collateral ligament (UCL) of the arm of the user during an arm motion.

Figure 1A:
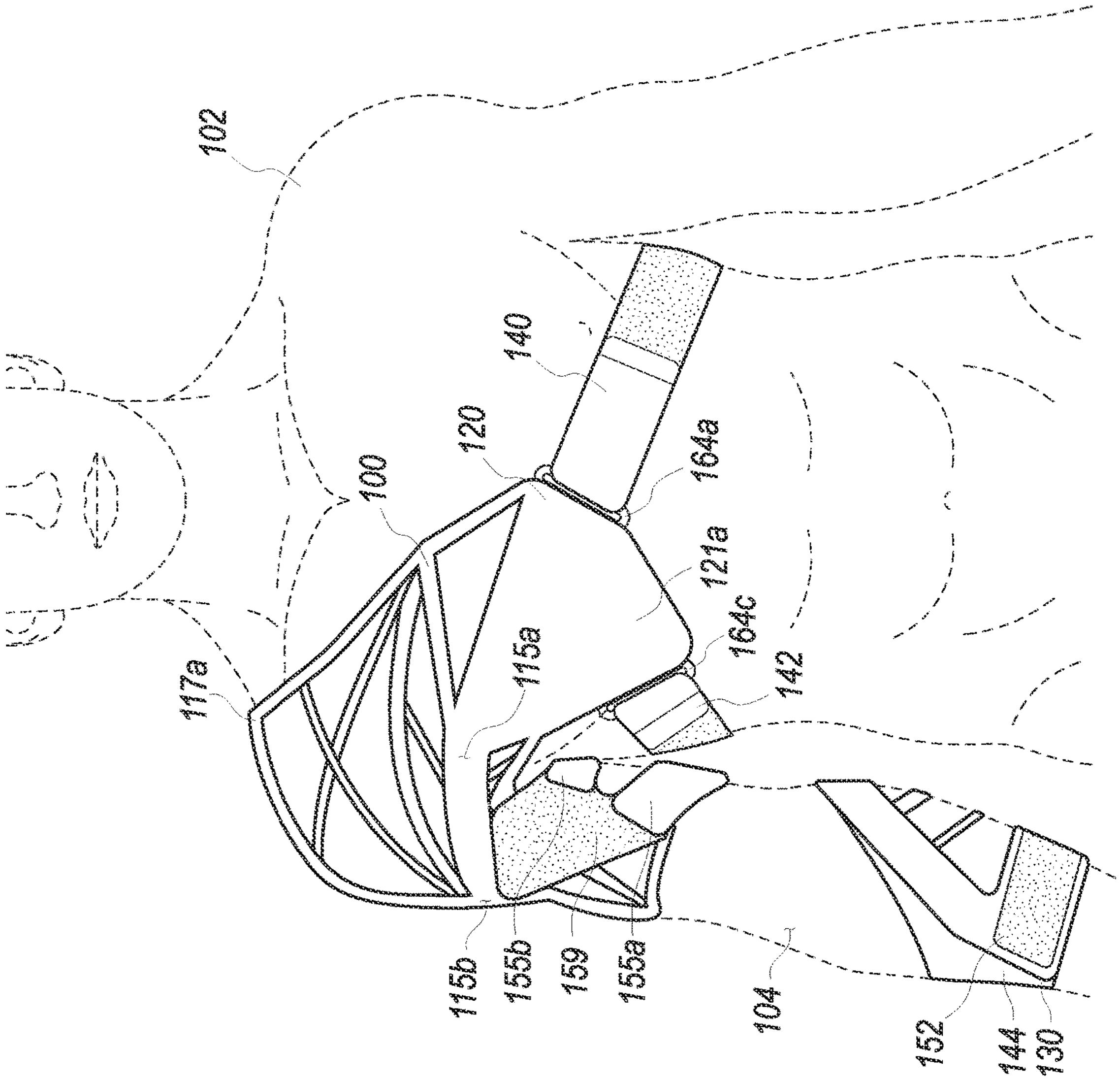
FIGS. 1A-1C illustrate an exemplary implementation of an arm sleeve that provides external assistance to the arm and shoulder during an arm motion; wherein the arm sleeve is being worn.
Figure 1B:
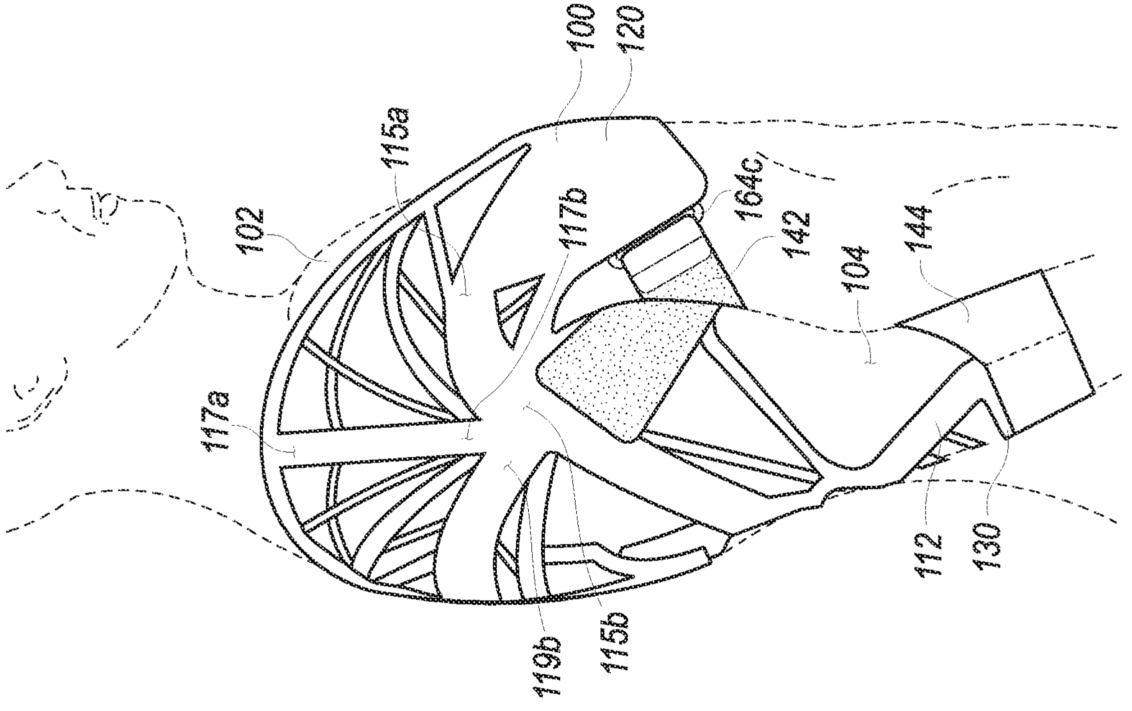
Figure 1C:
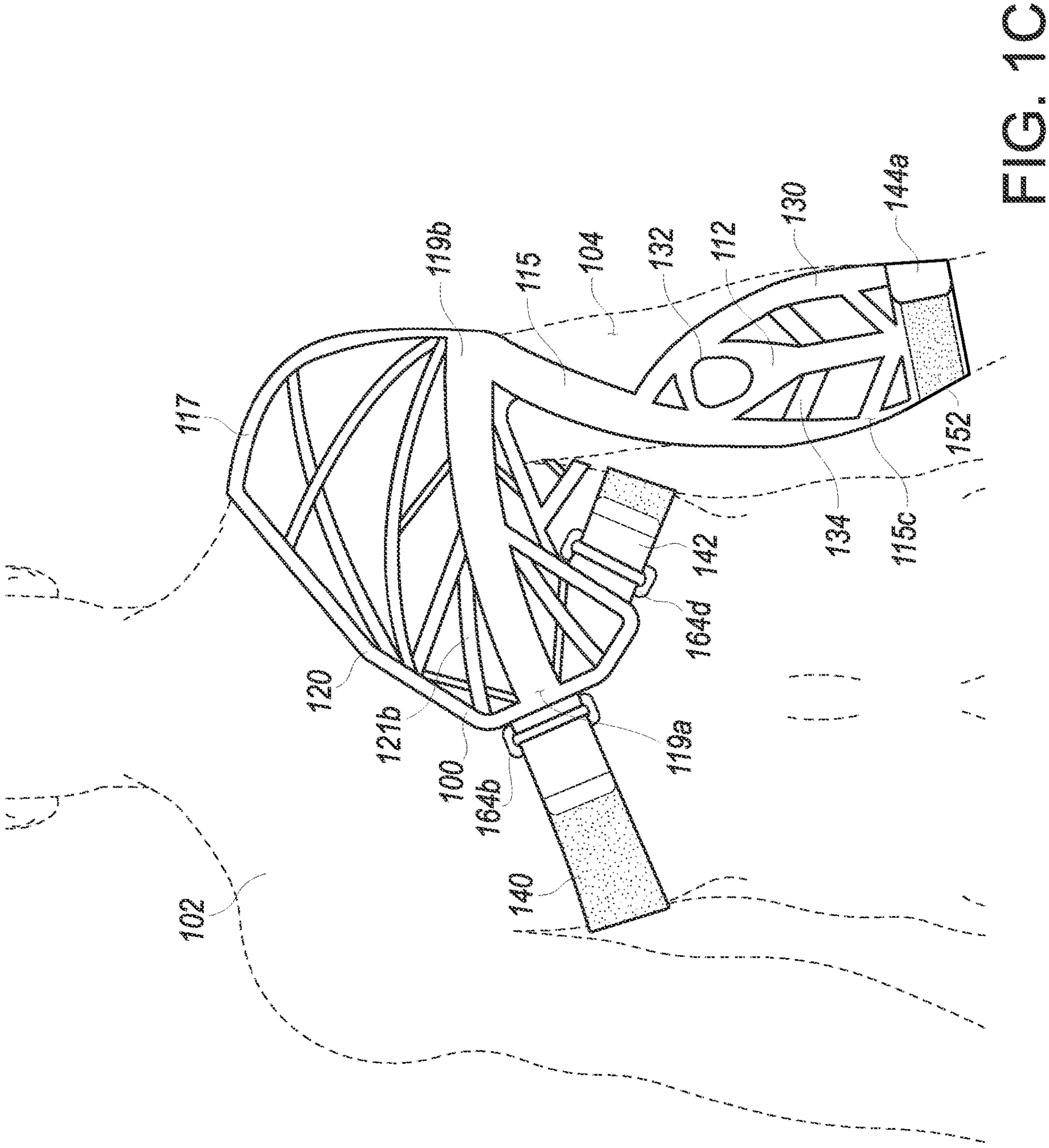

As shown in FIGS. 1A-1C, the arm sleeve 100 is configured to be worn on the throwing arm 104 of a user 102. While the implementation of the arm sleeve 100 shown in FIGS. 1A-1C is configured to be worn on the right arm 104, the arm sleeve 100 may be configured and adapted to be worn on the left arm if desired.

Figure 2A:
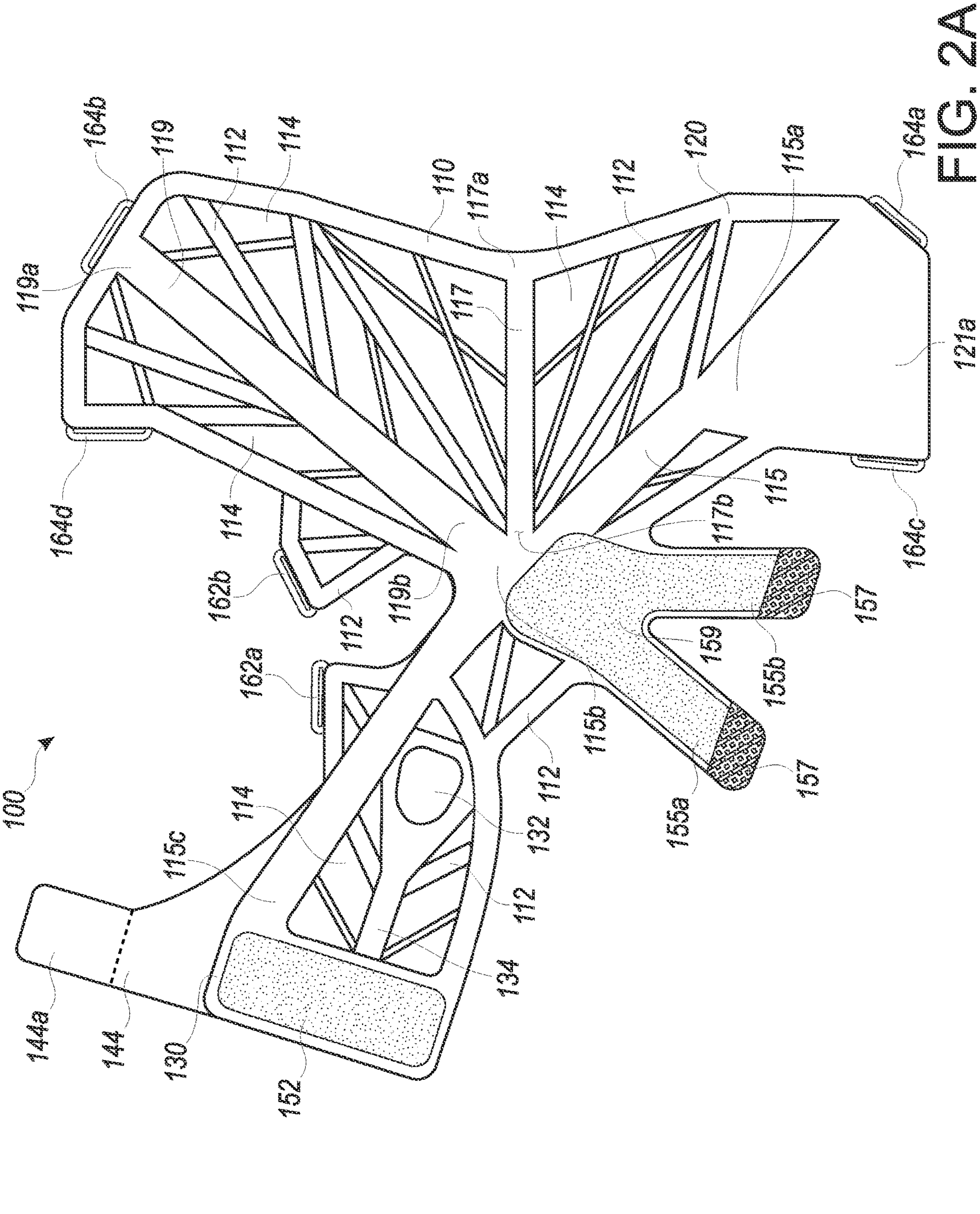
FIGS. 2A and 2B illustrate the arm sleeve shown in FIGS. 1A-1C, laid flat.
Figure 2B:
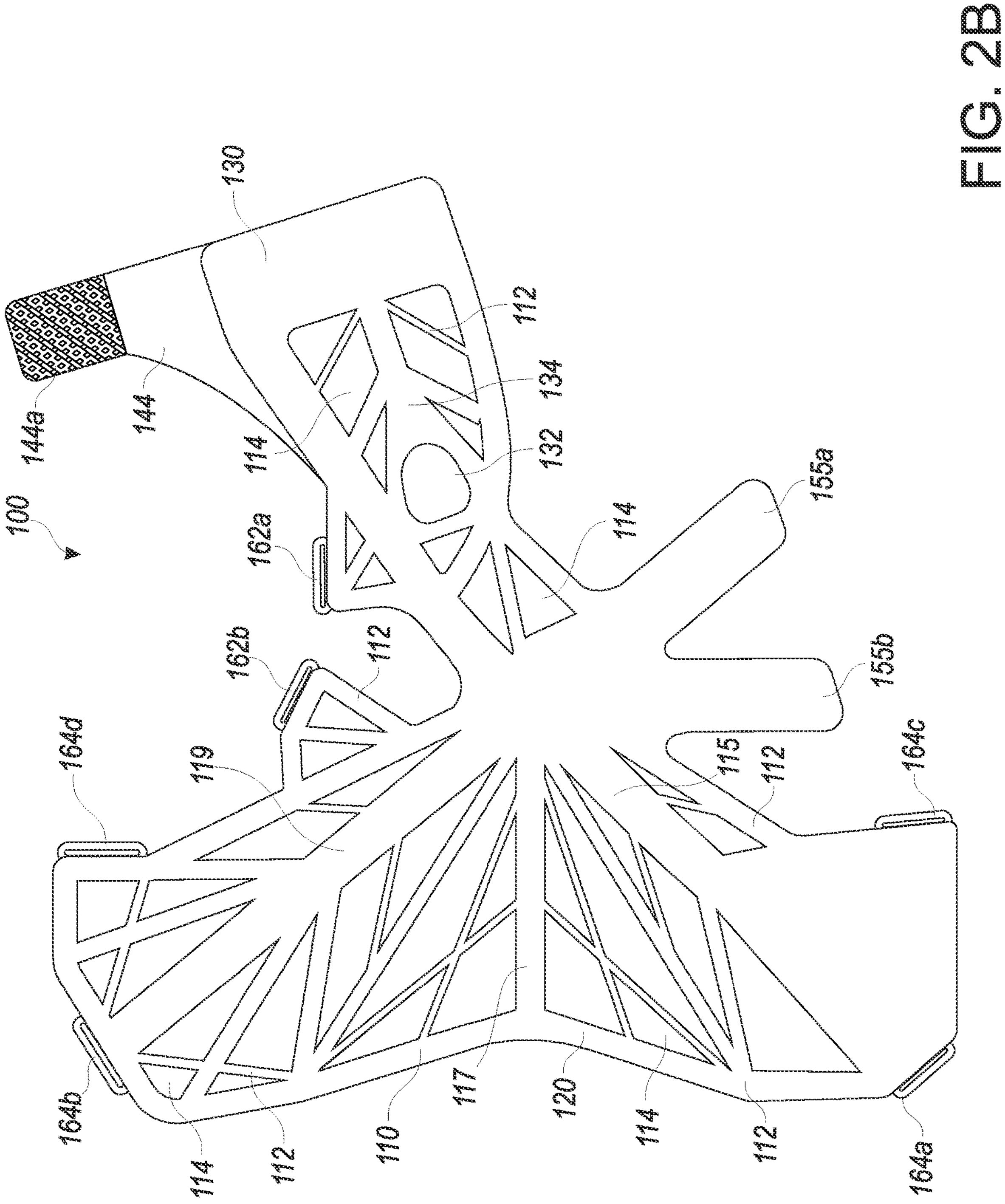

As shown in FIGS. 2A and 2B, in some implementations, the arm sleeve 100 comprises a framework 110 that includes a torso portion 120 configured to be attached to the torso of a user and an arm portion 130 configured to cover at least a portion of the throwing arm of the user while the arm sleeve 100 is being worn. In the implementation shown in FIGS. 1A-1C, the arm portion 130 comprises a sleeve that extends below the elbow joint of the user's throwing arm and a forearm strap 144 configured to secure the distal end of the arm portion 130 about the forearm of the user's throwing arm. The arm sleeve 100 may further comprise two torso straps 140, 142 configured to adjustably position the torso portion 120 on the torso of the user (see, e.g., FIGS. 1A-1C).

As shown in FIGS. 2A and 2B, the framework 110 of the arm sleeve 100 is formed from one or more elastomeric materials such that the framework 110 is expandable and recoverable. As used herein, "elastomeric material" refers to "a material that is capable of being easily expanded and resuming former shape." Something that has the ability to resume its former shape after expansion or compression is referred to herein as being "recoverable." Also, something that is expandable and recoverable may be referred to herein as being "elastically stretchable." The framework 110 of the arm sleeve 100 is flexible and is capable of conforming to the general area of the body that its positioned against without substantial stretching; however, the framework 110 of the arm sleeve 100 may need to be stretched in order to conform to the general area of the body that it is positioned against. As used herein, "flexible" refers to "the ability to bend freely and repeatedly without breaking."

In some implementations, the framework 110 of the arm sleeve 100 is a unitary construction of interconnected elastic members 112, 115, 117, 119 that define permanent openings 114 therebetween (see, e.g., FIGS. 1A and 2A). In some implementations, the openings 114 of the framework 110 may be cut-outs, slits, etc. While the interconnected elastic members 112, 115, 117, 119 of the framework 110 generally convey tensional forces from any one member of the framework 110 to the other members, tensional forces of particular elastic members (e.g., 115, 119) are correlated with tensional forces of particular torso straps (e.g., 140, 142) due to proximity and directional arrangement of the elastic members.

In some implementations, a first elastic member 115 of the framework 110 includes a first end 115*a* that extends from the front side 121*a* of the torso portion 120, across the front of the arm portion 130, to a second area 115*b* located on the arm portion 130 (see, e.g., FIGS. 1A and 1B). The second area 115*b* of the first elastic member 115 is superior to the bicep of the throwing arm of the user (see, e.g., FIG. 1B). The first elastic member 115 continues across the triceps area, past the elbow joint, to a second end 115*c*. The second end 115*c* is located near the distal end of the arm portion 130, at approximately the mid-forearm of the user (see, e.g., FIG. 1C). The second end 115*c* of the first elastic member 115 is a part of the interconnected elastic members (e.g., 112) that make up the forearm segment 134 of the arm portion 130. In some implementations, the second end 115*c* of the first elastic member 115 extends medially onto an area that corresponds to the mid-forearm of the user's throwing arm (see, e.g., FIG. 1C).

The first elastic member 115 of the arm sleeve 100 is configured to play an active part throughout an overhead throwing motion. During the early cocking phase to the late cocking phase, the first elastic member 115 is stretched, storing elastic energy. During these phases of the throwing motion, the upper extremity of the user's throwing arm assumes the position of flexion, abduction, external rotation, and horizontal abduction. As the upper extremity of the user's throwing arm moves during the early cocking phase and the late cocking phase, certain muscles stretch and thereby store elastic energy. Specifically, the internal rotators (e.g., the subscapularis, teres major, pectoralis major) and horizontal adductors (e.g., pectoralis major) of the user's shoulder. The elastic energy stored by the arm sleeve 100, specifically the first elastic member 115, and other connected members 112, can now contribute to the acceleration of the overhead throwing motion by releasing stored elastic energy to assist the user's muscles during rotation and horizontal adduction of the shoulder.

Also, in some implementations, the second end 115*c* of the first elastic member 115, and the forearm segment 134 as a whole, is configured to restrict the end-range external rotation of the shoulder at peak late cocking phase and thereby contribute to a decrease in distraction (medially) and compression (laterally) forces placed on the elbow joint.

As shown in FIGS. 1C, 2A, and 2B, the forearm segment 134 of the arm sleeve 100 may include an opening 132 for receiving the joint protuberance of an elbow. In this way, the arm portion 130 of the arm sleeve 110 may be configured to potentiate the elbow joint. The opening 132 is defined in and bounded by the framework 110 of the arm sleeve 100.

In some implementations, a second elastic member 117 of the framework 110 includes a first end 117*a* that extends from an edge of the torso portion 120 corresponding to the shoulder of the user's throwing arm to a second end 117*b* located on the arm portion 130. The second end 117*b* of the second elastic member 117 overlays at least a portion of the bicep of the user's throwing arm (see, e.g., FIG. 1B). The second end 117*b* of the second elastic member 117 intersects with the second area 115*b* of the first elastic member 115.

The second elastic member 117 of the arm sleeve 100 runs in the same direction as the supraspinatus and middle deltoid of the shoulder and is configured to decrease the concentric contraction force necessary for shoulder abduction during the cocking phase of a throwing motion. This is important because fatigue of the supraspinatus muscle decreases the force present to properly couple the glenohumeral joint (the shoulder joint). Deltoid contraction will increase when the supraspinatus muscle is fatigued; this increase in deltoid contraction will superiorly translate the glenohumeral joint and thereby cause, or at least contribute to, shoulder impingement.

In some implementations, a third elastic member 119 of the framework 110 includes a first end 119*a* that extends from the back side 121*b* of the torso portion 120, across the back of the arm portion 130 to a second end 119*b*, located on the arm portion 130, that corresponds to the triceps of the user's throwing arm (see, e.g., FIG. 1C). The second end 119*b* of the third elastic member 119 intersects with the second area 115*b* of the first elastic member 115 and the second end 117*b* of the second elastic member 117, thereby forming a junction.

The third elastic member 119 of the arm sleeve 100 is configured to assist eccentrically contracting muscles (e.g., posterior deltoid, teres minor, lower trapezius, infraspinatus, and rhomboids) during the deceleration phase of a throwing motion by preventing the upper extremity of the user's throwing arm from overextending. The third elastic member 119 stretches (or lengthens) as the upper extremity of the user's throwing arm moves into extension and the shoulder rotates. In this way, the third elastic member 119 minimizes the amount of valgus torque, and varus torque, that is placed on the soft medial structures of the elbow joint.

The interconnected elastic members 112, 115, 117, 119 of the framework 100 may have any desired width, thickness, or elasticity. For example, the width, thickness, and elasticity of the first, second, or third elastic members 115, 117, 119 of the arm sleeve 100 may vary depending on the size, age, gender, extent of injury, etc. of the intended user.

In some implementations, one or more of the interconnected elastic members 112, 115, 117, 119 of the framework 110 may be made of the same or different materials, may be the same or different thickness or width, may have the same or different amounts (or moduli) of elasticity, etc. as desired and in accordance with the implementations of the arm sleeve 100 disclosed herein.

In some implementations, the framework 110 of the arm sleeve 100 may be made of an elastomer material, for example, a silicone rubber. The tensile strength of the elastomer used to form the framework 110 may affect (e.g., increase or decrease) the speed of a user's throw. In some implementations, the framework 110 of the arm sleeve 100 may be made of an elastomer material other than silicone rubber.

As shown in FIG. 2A, in some implementations, the arm sleeve 100 may include two connectors 155*a*, 155*b* (collectively 155) thereon that are configured to adjustably secure the proximal end of the arm portion 130 on the upper extremity of the user's throwing arm. The example connectors 155 each include hook-and-loop fasteners capable of adjustably securing a distal end 157 thereof to a proximal end 159. The distal end 157 of each connector 155*a*, 155*b* is configured to pass through an opening in a complementary buckle 162*a*, 162*b* extending from the opposite side of the arm sleeve 100 framework 110, prior to being folded back on itself and secured to the proximal end 159. In this way, when donning the arm sleeve 100, the proximal end of the arm portion 130 can be secured about the upper extremity of the user's throwing arm (see, e.g., FIG. 1A). In some implementations, snaps, hooks, or other fasteners capable of adjustably securing the distal end 157 of a connector 155*a*, 155*b* to its proximal end 159 may be used. In some implementations, a connector 155*a*, 155*b* may be any appropriate mechanism suitable for securing the proximal end of the arm portion 130 about the upper extremity of the user's throwing arm.

As shown in FIGS. 2A and 2B, in some implementations, the forearm strap 144 extends from an edge of the forearm segment 134 of the arm portion 130 and includes a tab 144*a* that extends from its distal end. The forearm strap 144 is configured to encircle the forearm of the user and the tab 144*a* is configured to be removably affixed to the distal portion of the forearm segment 134 (see, e.g., FIGS. 1A-1C). In some implementations, hook-and-loop fasteners may be used to secure the tab 144*a* of the forearm strap 144 to the distal portion of the forearm segment 134. In particular, the tab 144*a* may include hooks 150 thereon that are configured to catch on loops 152 positioned adjacent the distal end of the arm portion 130 (see, e.g., FIGS. 2A and 2B). In use, the forearm strap 144 is wrapped about the forearm of the user and, once the desired fit is achieved, the tab 144*a* is secured to the distal portion of the forearm segment 134 via the hook-and-loop fasteners 150, 152. In this way, the user may adjust the fit of the forearm segment 134 when donning the arm sleeve 100. In some implementations, other fasteners, or fastening mechanisms, such as snaps, buttons, etc. may be used to secure the tab 144*a* of the forearm strap 144 to the distal portion of the forearm segment 134.

As shown in FIGS. 1A and 1C, in some implementations, the first adjustable torso strap 140 may extend between a first buckle 164*a* secured to the front side 121*a* of the torso portion 120 and a second buckle 164*b* secured to the backside 121*b* of the torso portion 120. In some implementations, the first buckle 164*a* may be in-line with the first end 115*a* of the first elastic member 115 and the second buckle 164*b* may be in-line with the first end 119*a* of the third elastic member 119. In this way, the tensional forces associated with the first elastic member 115 and the third elastic member 119 of the framework 110 may be correlated with tensional forces of the first torso strap 140.

In some implementations, shifting (or translating) the front side 121*a* of the torso portion 120 toward the contralateral side (side opposite the throwing arm), and using the first adjustable torso strap 140 to secure it in position, increases the tension of (or lengthens) the elastic members of the framework 110, the first elastic member 115 in particular. This will increase the muscular assistance provided by the arm sleeve 100 during the acceleration phase of a throwing motion. Alternatively, shifting (or translating) the front side 121*a* of the torso portion 120 towards the ipsilateral side (i.e., towards the throwing arm), and using the first adjustable torso strap 140 to secure it in position, decreases the tension of (or shortens) the elastic members of the framework 110 positioned on the posterior side of the user, the third elastic member 119 in particular. This will increase the muscular assistance provided by the arm sleeve 100 during the deceleration phase of a throwing motion.

As shown in FIGS. 1A and 1C, in some implementations, the second adjustable torso strap 142 may extend between a third buckle 164*c* secured to the front side 121*a* of the torso portion 120 and a fourth buckle 164*d* secured to the backside 121*b* of the torso portion 120.

As shown in FIGS. 1A-1C, in some implementations, when the arm sleeve 100 is being worn, the loops formed by the adjustable torso straps 140, 142 are positioned between the user's arms and body.

Figure 3A:
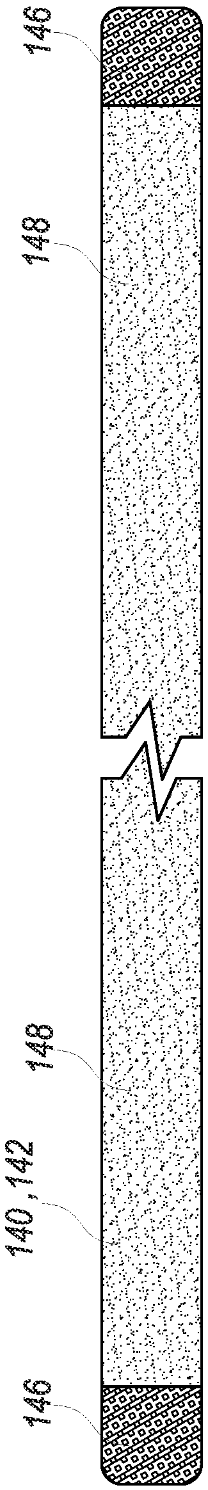
FIGS. 3A-3C illustrate an exemplary torso strap used to position the arm sleeve shown in FIGS. 2A and 2B on the torso of a person. A symbolic break in the length is represented by a centrally located pair of adjacent lines.
Figure 3B:
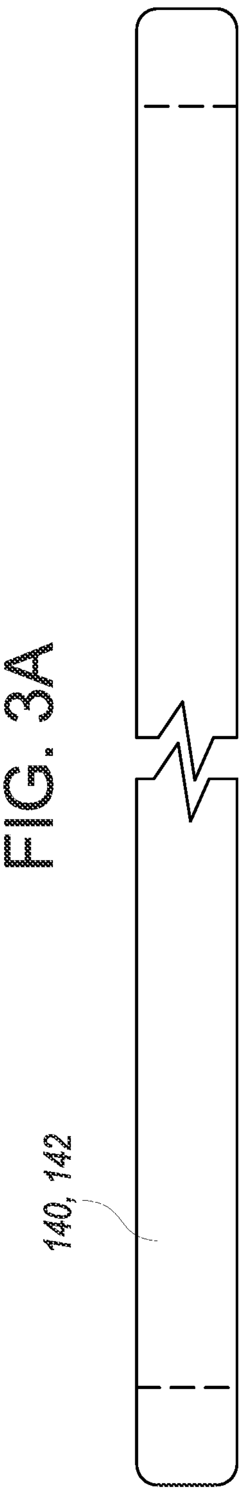
Figure 3C:
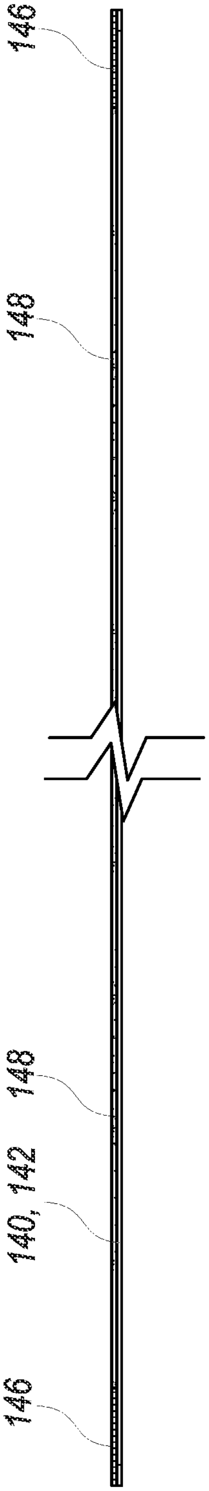

FIGS. 3A-3C illustrate the adjustable torso straps 140, 142 used to position the arm sleeve 100 on the torso of a user, wherein the centrally located pair of adjacent lines are included for indicating that no particular length is being specified. Other than length, the torso straps 140, 142 can be identically constructed. In some implementations, each end of an adjustable torso strap 140, 142 may be secured about its corresponding buckle (e.g., 164*a*, 164*b*, 164*c*, 164*d*) through the use of hook-and-loop fasteners. In particular, a first end and a second end of each adjustable torso strap 140, 142 may include hooks 146 thereon that are configured to catch on loops 148 positioned along the length of each strap. Each end of an adjustable torso strap 140, 142 is configured to pass through an opening in its complementary buckle (e.g., 164*a*, 164*b*, 164*c*, 164*d*), prior to being folded back on itself so that the hooks 146 catch on the loops 148. This allows the user to adjust the fit of the torso portion 120 when donning the arm sleeve 100. In some implementations, other fasteners, or fastening mechanisms, may be used to secure each end of an adjustable torso strap 140, 142 to its complementary buckle (e.g., 164*a*, 164*b*, 164*c*, 164*d*).

The adjustable torso straps 140, 142 may be made of nylon. In some implementations, the adjustable torso straps 140, 142 may be made of any suitable material that is selected in accordance with the implementations of the arm sleeve 100 disclosed herein.

Implementations of the arm sleeve 100 may be provided in varying sizes and/or configurations to accommodate the size, age, and/or gender of the user.

FIGS. 4A-4C and 5A-5B illustrate another example implementation of an arm sleeve 200 according to the principles of the present disclosure. In some implementations, the arm sleeve 200 is similar to the arm sleeve 100 discussed above but the framework 210 is encased by a neoprene cover 270. However, the principles and configuration of the first elastic member 215, the second elastic member 217, and the third elastic member 219 of the framework 210 are the same as, or at least similar to, the first elastic member 115, the second elastic member 117, and the third elastic member 119 discussed above in connection with the arm sleeve 100 shown in FIGS. 2A and 2B.

Figure 6:
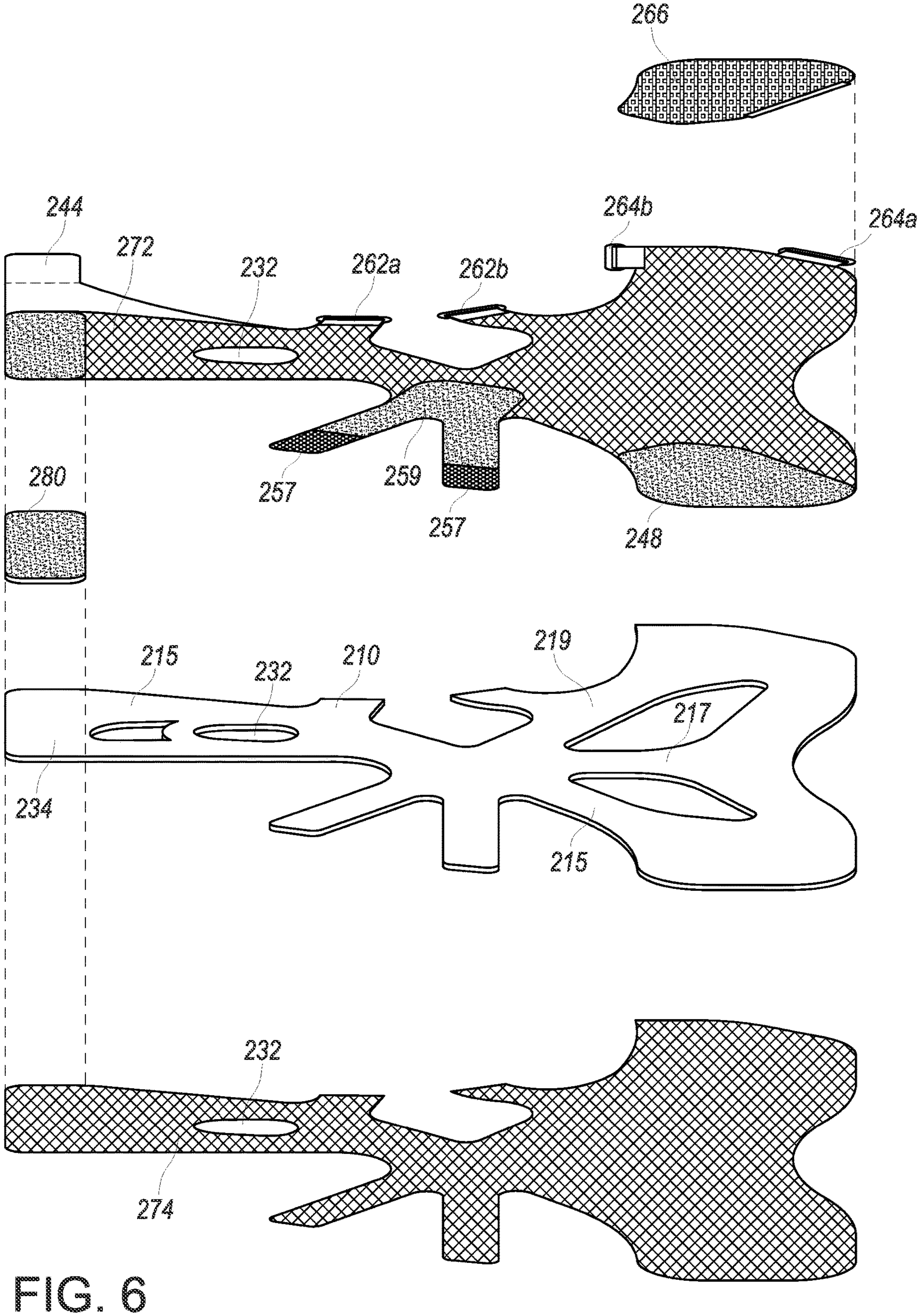
FIG. 6 illustrates an exploded view of the arm sleeve shown in FIGS. 5A and 5B.

As shown in FIG. 6, in some implementations, the neoprene cover 270 comprises a first piece (or layer) of material 272 configured to overlay an exterior side of the framework 210 and a second piece (or layer) of material 274 configured to overlay an interior side of the framework 210. In some implementations, the two pieces of neoprene material 272, 274 may be joined together along their mutual edges using any suitable method known to those of ordinary skill in the art (e.g., stitching). In this way, the framework 210 of the arm sleeve 200 may be encased. In some implementations, a mesh neoprene cover 270 is used.

Figure 5A:
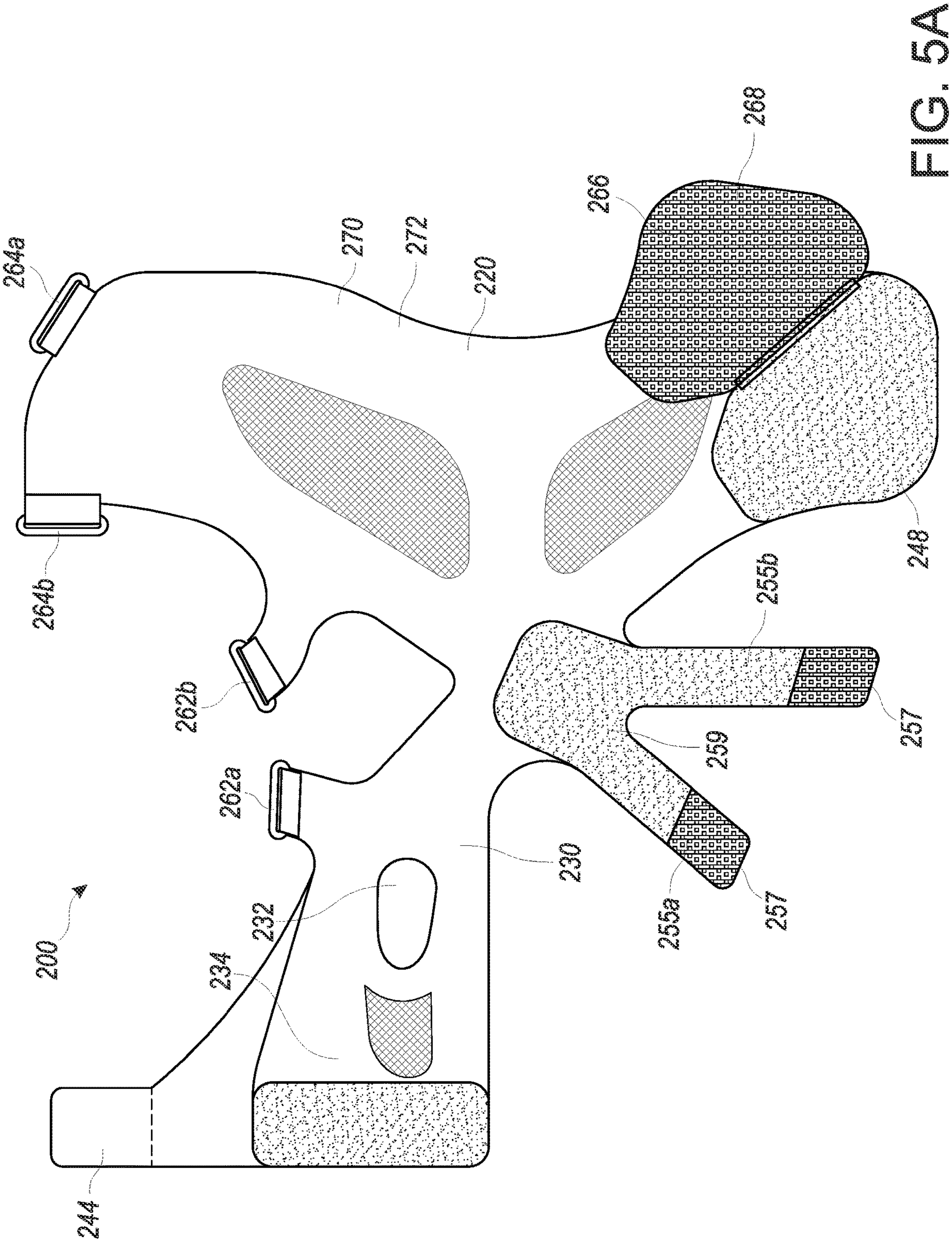
FIGS. 5A and 5B illustrate the arm sleeve shown in FIGS. 4A-4C, laid flat.
Figure 5B:
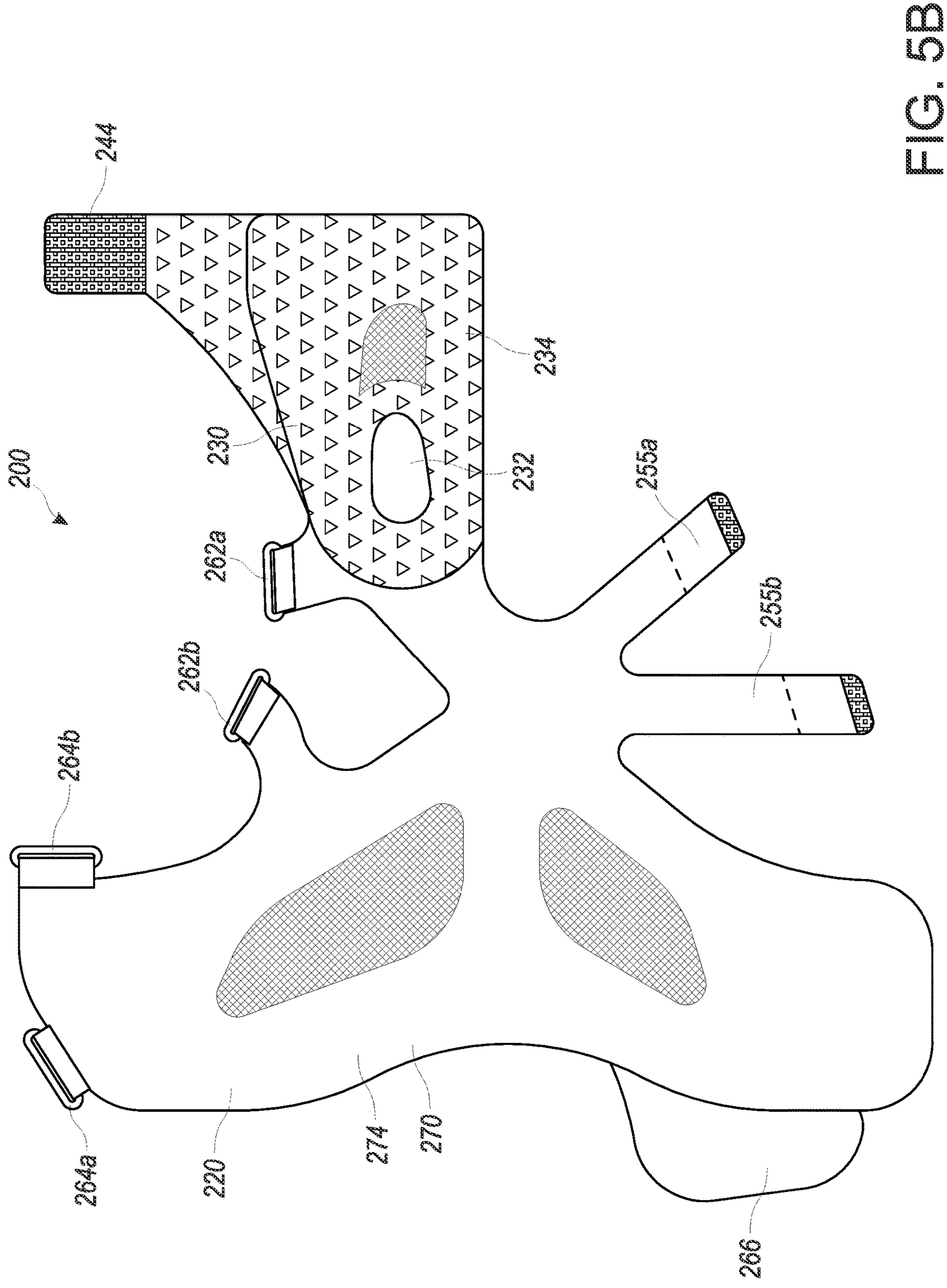

As shown in FIGS. 5A, 5B, and 6, in some implementations, the opening 232 for receiving the joint protuberance of an elbow extends through the forearm segment 234 of the neoprene cover 270 and the framework 210 of the arm sleeve 200.

As shown in FIG. 5B, in some implementations, the interior side of the forearm segment 234 of the arm sleeve 200 may include a plurality of silicone dots 280 (or silicone grip print) thereon. In this way, the forearm segment 234 of the arm portion 230 may be prevented from sliding (or slipping) on the user's skin during an arm motion. In some implementations, the silicone dots 280 are affixed to the neoprene cover 270 of the arm sleeve 200. In some implementations, the interior side of the forearm segment 234 of the arm sleeve 200 may not have any silicone dots 280 thereon.

As shown in FIG. 6, in some implementations, a stiffening insert 280 may be positioned on the distal end of the forearm segment 234, between the framework 210 and the neoprene cover 270. In some implementations, the stiffening insert 280 may be a rectangular layer of flexible plastic positioned and configured to assist with comfortably securing the distal end of the arm portion 230 about the user's forearm. In particular, the stiffening insert 280 may cup (or conform to) the portion of the forearm that it's in contact with and thereby preserve circulation to the limb (i.e., the throwing arm).

As shown in FIG. 6, in some implementations, the connectors 255*a*, 255*b* of the arm sleeve 200 are similar to the connectors 155*a*, 155*b* discussed above but the hook-and-loop fasteners 257, 259 are located on the first layer 272 of the neoprene cover 270. Except as noted above, the principles and configuration of the connectors 255*a*, 255*b*, and their corresponding buckles 262*a*, 262*b*, are the same as the connectors 155*a*, 155*b*, and their corresponding buckles 162*a*, 162*b*, discussed above in connection with the arm sleeve 100 shown in FIGS. 2A and 2B.

As shown in FIGS. 5A and 5B, the principles and configuration of the forearm strap 244 are the same as, or substantially similar to, the forearm strap 144 discussed above in connection with the arm sleeve 100 shown in FIGS. 2A and 2B. In some implementations, the forearm strap 244 may extend from the forearm segment of the first layer 272 of the neoprene cover 270 instead of the framework 210.

As shown in FIG. 6, in some implementations, the buckles 264*a*, 264*b*, used in conjunction with the adjustable torso straps 240, 242 to adjustably position the torso portion 220 of the arm sleeve 200 on the torso of the user are secured to the neoprene cover 270, specifically, the first layer 272 thereof. Except as described below, the buckles 264*a*, 264*b* and the adjustable torso straps 240, 242 of the arm sleeve 200 are similar to, and perform the same function as, the buckles 164*a*, 164*b*, 164*c*, 164*d* and the adjustable torso straps 140, 142 discussed above in connection with the arm sleeve 100 shown in FIGS. 2A and 2B.

Figure 4A:
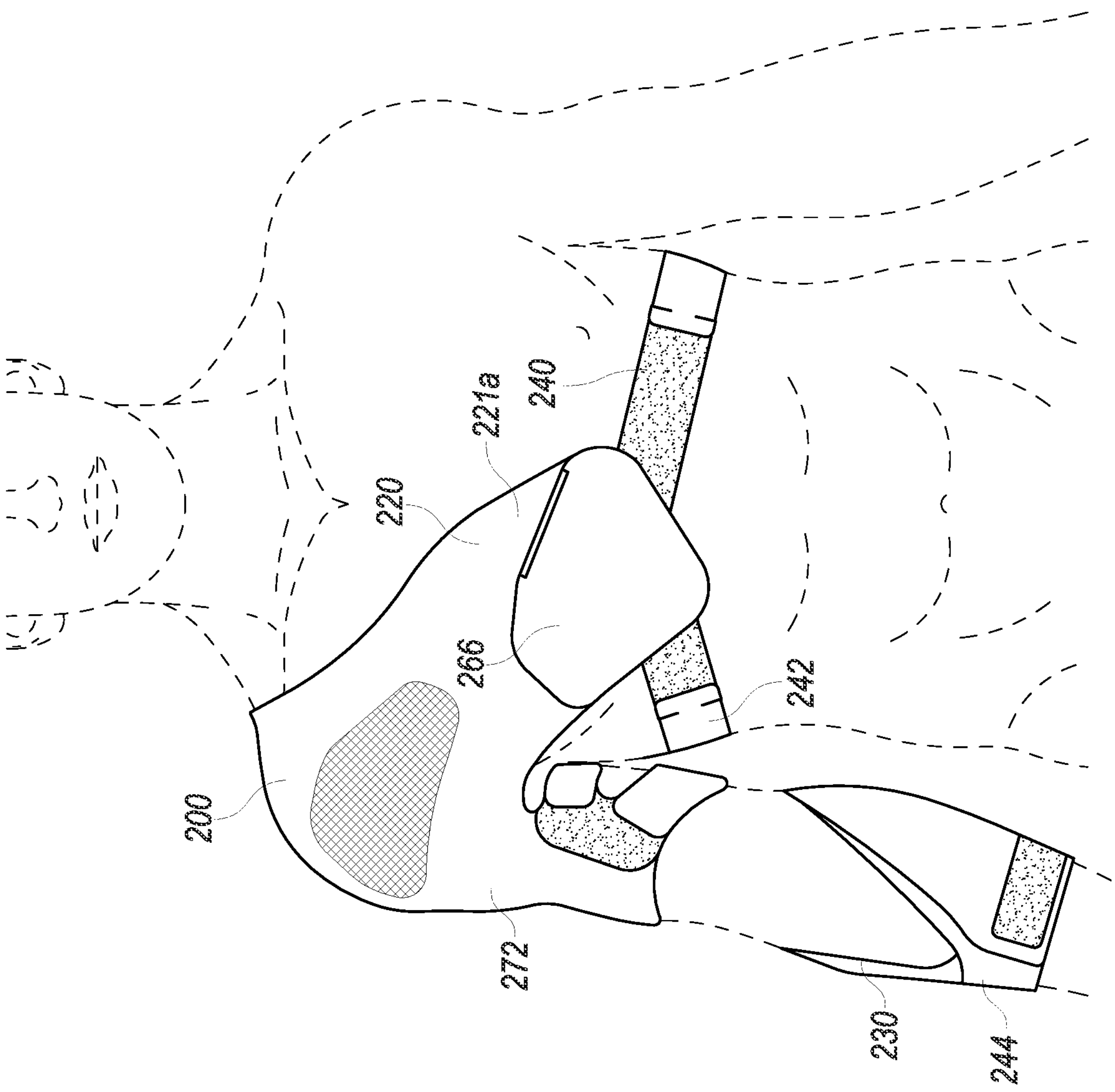
FIGS. 4A-4C illustrate another exemplary implementation of an arm sleeve that provides external assistance to the arm and shoulder during an arm motion, wherein the arm sleeve is being worn.
Figure 4B:
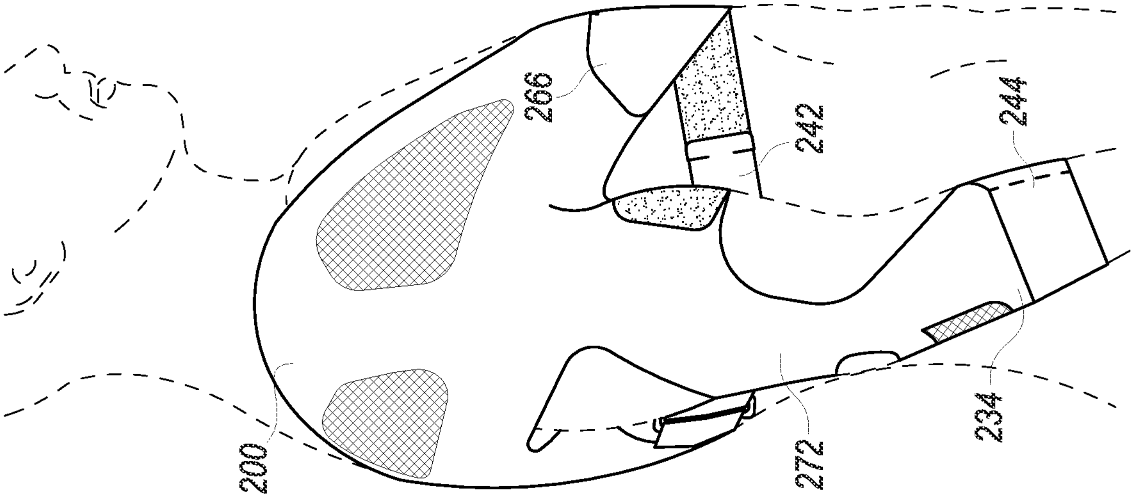
Figure 4C:
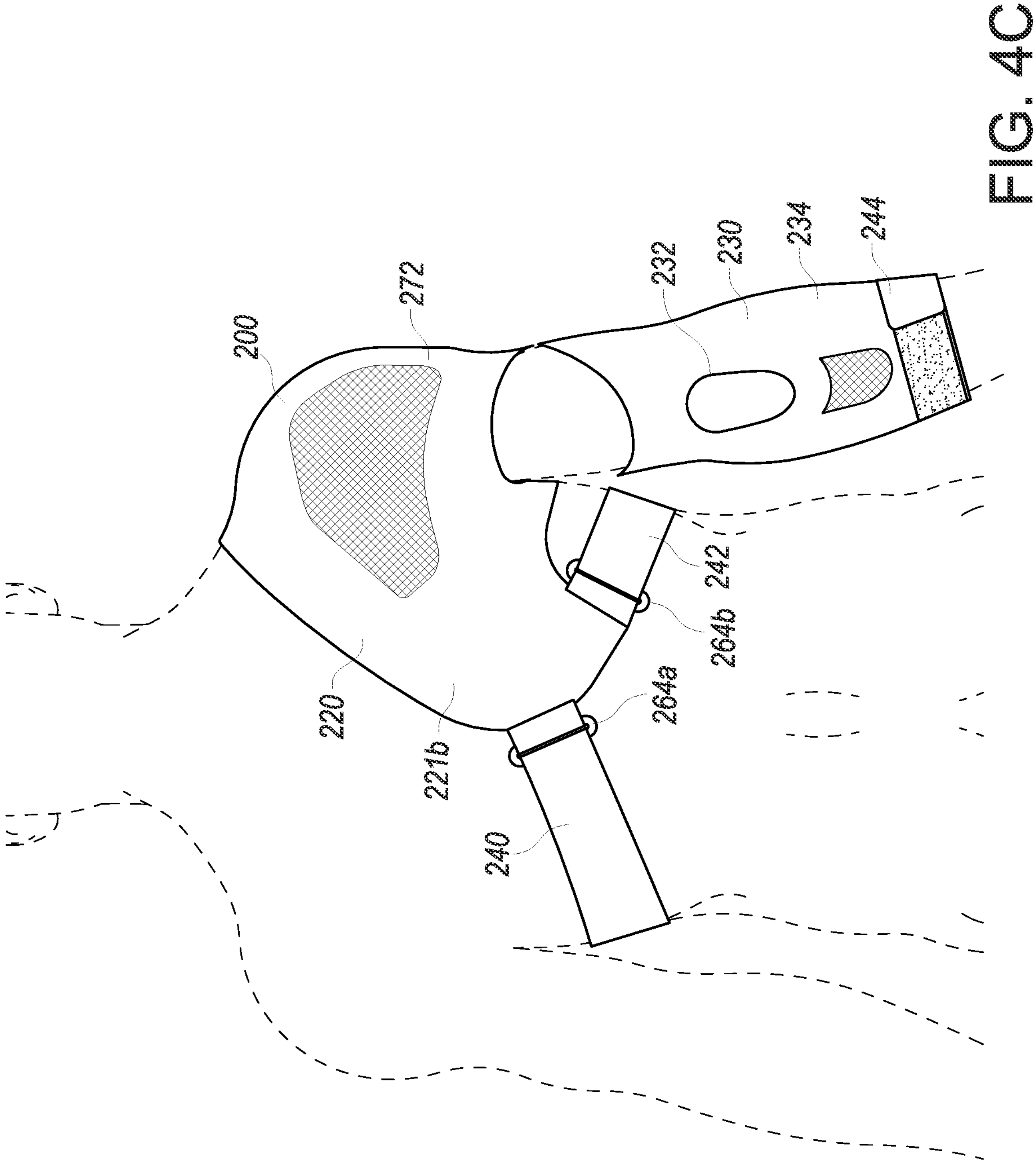

As shown in FIGS. 4A and 4C, in some implementations, the first adjustable torso strap 240 may extend from the front side 221*a* of the torso portion 220 to a first buckle 264*a* secured to the backside 221*b* of the torso portion 220.

As shown in FIGS. 4A-4C, in some implementations, the second adjustable torso strap 242 may extend from the front side 221*a* of the torso portion 220 to a second buckle 264*b* secured to the backside 221*b* of the torso portion 220.

Figures 7A, 7B, 7C:
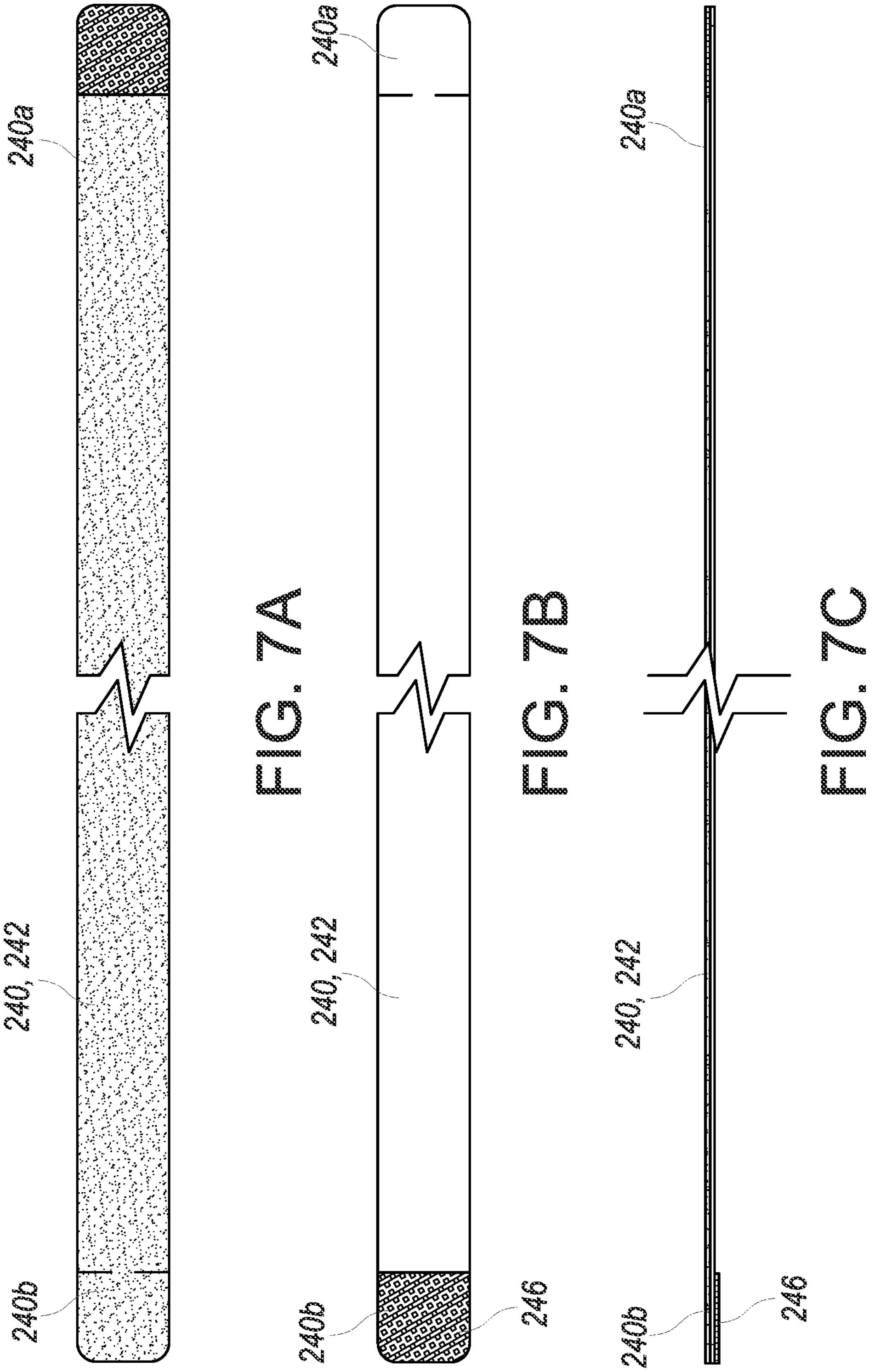
FIGS. 7A-7C illustrate an exemplary torso strap used to position the arm sleeve shown in FIGS. 5A and 5B on the torso of a person. A symbolic break in the length is represented by a centrally located pair of adjacent lines.

FIGS. 7A-7C illustrate the adjustable torso straps 240, 242 used to position the arm sleeve 200 on the torso of a user, wherein the centrally located pair of adjacent lines are included for indicating that no particular length is being specified. Other than length, the torso straps 240, 242 can be identically constructed. In some implementations, the first end 240*a* and the second end 240*b* of each adjustable torso strap 240, 242 may be secured about a corresponding buckle (i.e., 264*a*, 264*b*) or to the front side 221*a* of the torso portion 220, respectively, through the use of hook-and-loop fasteners. The first end 240*a* of each adjustable torso strap 240, 242 may be secured to its corresponding buckle 264*a*, 264*b* in the same, or a similar, manner as discussed above in connection with the arm sleeve 100 shown in FIGS. 1A-1C. In some implementations, the second end 240*b* of each adjustable torso strap 240, 242 may include hooks 246 on one side thereof that are configured to catch on loops 248 positioned on the front side 221*a* of the torso portion 220 (see, e.g., FIG. 4A). In this way, the second end 240*b* of an adjustable torso strap 240, 242 may be secured to the front side 221*a* of the torso portion 220.

As shown in FIGS. 4A, 5A, and 6, in some implementations, the torso portion 220 of the arm sleeve 200 may include a cover flap 266 that is configured to overlay the fastener(s) 248 positioned on the front side 221*a* thereof, and to capture the second end 240*b* of each adjustable torso strap 240, 242 therebetween. In some implementations, the cover flap 266 may be attached to the torso portion 220 by a hinge and include hooks 268 on an interior side thereof that are complementary to the loops 248 located on the front side 221*a* of the torso portion 220. In this way, the cover flap 266 can be used to further secure the second end 240*b* of each adjustable torso strap 240, 242 to the front side 221*a* of the torso portion 220.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. An arm sleeve configured to provide external assistance to an arm and shoulder of a user during an arm motion, the arm sleeve comprising:

an elastomeric cover;

a framework that is encased by the elastomeric cover, the framework includes a torso portion configured to be attached to the torso of the user and an arm portion configured to receive at least a portion of the arm of the user, the framework is a unitary construction of interconnected elastic members;

the interconnected elastic members of the framework include a first elastic member configured to store and release elastic energy to assist muscles of the user, the first elastic member including a first end, a second area, and a second end, wherein the first end of the first elastic member extends from a front side of the torso portion, across a front side of the arm portion to the second area, wherein the second area is part of the arm portion, wherein the first elastic member is configured to continue directly from the second area to spiral posteriorly across a triceps area of the arm, past an elbow joint of the arm, and anteriorly to the second end, wherein the second end is located near a distal end of the arm portion at a mid-forearm of the arm when the arm sleeve is being worn;

the interconnected elastic members of the framework include a second elastic member with a first end and a second end, wherein the first end of the second elastic member extends from an edge of the torso portion that is configured to overlay the shoulder of the arm to the second end, wherein the second end is part of the arm portion and superior to the bicep of the arm when the arm sleeve is being worn; and the interconnected elastic members of the framework include a third elastic member with a first end and a second end, wherein the first end of the third elastic member extends from a back side of the torso portion, across a back side of the arm portion to the second end, wherein the second end is part of the arm portion and is joined to the second area of the first elastic member;

wherein each of the first elastic member and the third elastic member extends separately from the front side and the back side of the torso portion, respectively, and converges at the second area; and wherein the first elastic member and the third elastic member are fixed relative to each other at the second area.

2. The arm sleeve of claim 1, wherein the second end of the first elastic member is configured to extend medially onto an area that overlays the mid-forearm of the arm and is a part of the interconnected elastic members that make up a forearm segment of the arm portion; wherein the second end of the second elastic member is configured to overlay at least a portion of the bicep of the arm; and wherein the second end of the third elastic member is configured to overlay at least a portion of the triceps of the arm.

3. The arm sleeve of claim 2, wherein the forearm segment of the arm portion includes an opening for receiving a joint protuberance of the elbow and is thereby configured to potentiate the elbow joint.

4. The arm sleeve of claim 2, wherein the forearm segment of the arm portion includes a stiffening insert configured to preserve circulation to the arm while the arm sleeve is being worn.

5. The arm sleeve of claim 1, wherein the elastomeric cover comprises at least one piece of material configured to overlay a first side of the framework and at least one piece of material configured to overlay a second side of the framework, the at least two pieces of material are joined together along their mutual edges to thereby encase the framework of the arm sleeve.

6. The arm sleeve of claim 5, wherein a forearm segment of the arm sleeve includes a stiffening insert configured to preserve circulation to the arm while the arm sleeve is being worn, the stiffening insert is positioned between a distal portion of the framework and the elastomeric cover.

7. The arm sleeve of claim 1, wherein the first elastic member, the second elastic member, and the third elastic member of the framework are operable to provide assistance to at least one muscle supporting an ulnar collateral ligament (UCL) of the arm of the user during the arm motion.

8. The arm sleeve of claim 1, wherein the elastomeric cover and the framework are flexible and capable of conforming to an area of the user's body that they are positioned against.

9. The arm sleeve of claim 1, wherein a forearm segment of the arm portion includes an opening for receiving a joint protuberance of the elbow and is thereby configured to potentiate the elbow joint.

10. The arm sleeve of claim 1, wherein a forearm segment of the arm portion includes a forearm strap, the forearm strap extends from an edge of the forearm segment and is configured to encircle the forearm of the user and thereby secure the distal end of the arm portion in position.

11. The arm sleeve of claim 1, further comprising two torso straps configured to adjustably position the torso portion of the arm sleeve on the torso of the user.

12. An arm sleeve configured to provide external assistance to an arm and shoulder of a user during an arm motion, the arm sleeve comprising:

a framework that includes a torso portion configured to be attached to the torso of the user and an arm portion configured to receive at least a portion of the arm of the user, wherein the framework is a unitary construction of interconnected elastic members;

the interconnected elastic members of the framework include a first elastic member configured to store and release elastic energy to assist muscles of the user, the first elastic member including a first end, a second area, and a second end, wherein the first end of the first elastic member extends from a front side of the torso portion, across a front side of the arm portion to the second area, wherein the second area is part of the arm portion, wherein the first elastic member is configured to continue directly from the second area to spiral posteriorly across a triceps area of the arm, past an elbow joint of the arm, and anteriorly to the second end, wherein the second end is located near a distal end of the arm portion at a mid-forearm of the arm when the arm sleeve is being worn;

the interconnected elastic members of the framework include a second elastic member with a first end and a second end, wherein the first end of the second elastic member extends from an edge of the torso portion that is configured to overlay the shoulder of the arm to the second end, wherein the second end is part of the arm portion and superior to the bicep of the arm when the arm sleeve is being worn; and the interconnected elastic members of the framework include a third elastic member with a first end and a second end, wherein the first end of the third elastic member extends from a back side of the torso portion, across a back side of the arm portion to the second end, wherein the second end is part of the arm portion and is joined to the second area of the first elastic member;

wherein each of the first elastic member and the third elastic member extends separately from the front side and the back side of the torso portion, respectively, and converges at the second area; and wherein the first elastic member and the third elastic member are fixed relative to each other at the second area.

13. The arm sleeve of claim 12, wherein the second end of the first elastic member is configured to extend medially onto an area that overlays the mid-forearm of the arm and is a part of the interconnected elastic members that make up a forearm segment of the arm portion; wherein the second end of the second elastic member is configured to overlay at least a portion of the bicep of the arm; and wherein the second end of the third elastic member is configured to overlay at least a portion of the triceps of the arm.

14. The arm sleeve of claim 13, wherein the forearm segment of the arm portion includes an opening for receiving a joint protuberance of the elbow and is thereby configured to potentiate the elbow joint.

15. The arm sleeve of claim 12, wherein the first elastic member, the second elastic member, and the third elastic member of the framework are operable to provide assistance to at least one muscle supporting an ulnar collateral ligament (UCL) of the arm of the user during the arm motion.

16. The arm sleeve of claim 12, wherein the framework is flexible and is capable of conforming to an area of the user's body that it is positioned against.

17. The arm sleeve of claim 12, wherein a forearm segment of the arm portion includes an opening for receiving a joint protuberance of the elbow and is thereby configured to potentiate the elbow joint.

18. The arm sleeve of claim 12, wherein a forearm segment of the arm portion includes a forearm strap, the forearm strap extends from an edge of the forearm segment and is configured to encircle the forearm of the user and thereby secure the distal end of the arm portion in position.

19. The arm sleeve of claim 12, further comprising two torso straps configured to adjustably position the torso portion of the arm sleeve on the torso of the user.

* * * * *